(12) United States Patent
Tomoshige et al.

(10) Patent No.: US 6,664,425 B2
(45) Date of Patent: Dec. 16, 2003

(54) PROCESS FOR PRODUCING 1,3-BIS(3-AMINOPHENOXY)BENZENE

(75) Inventors: Naoki Tomoshige, Sodegaura (JP); Yasuhiro Nukii, Omuta (JP); Masaru Wada, Omuta (JP); Koju Okazaki, Sodegaura (JP); Hidetoshi Hayashi, Omuta (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 10/220,708

(22) PCT Filed: Feb. 13, 2002

(86) PCT No.: PCT/JP02/01183

§ 371 (c)(1),
(2), (4) Date: Sep. 5, 2002

(87) PCT Pub. No.: WO02/064544

PCT Pub. Date: Aug. 22, 2002

(65) Prior Publication Data

US 2003/0078454 A1 Apr. 24, 2003

(30) Foreign Application Priority Data

Feb. 13, 2001 (JP) .......................................... 2001-35708
Jan. 10, 2002 (JP) .......................................... 2002-3175

(51) Int. Cl.$^7$ .............................................. C07C 213/00
(52) U.S. Cl. ....................................................... 564/430
(58) Field of Search ........................................ 564/430

(56) References Cited

U.S. PATENT DOCUMENTS 4,222,962 A 9/1980 Pellegrini, Jr.

FOREIGN PATENT DOCUMENTS

| EP | 0 034 402 A2 | 8/1981 |
| JP | 5-271167 A | 10/1993 |
| JP | 7-309817 A | 11/1995 |

*Primary Examiner*—Samuel Barts
(74) *Attorney, Agent, or Firm*—Burns, Doane, Swecker & Mathis, LLP

(57) ABSTRACT

1,3-Bis(3-aminophenoxy)benzene effective, for example, as a raw material for highly heat-resistant polyimide is produced industrially at a high yield by a reaction between 1,3-difluorobenzene and an alkali metal salt of 3-aminophenol.

4 Claims, No Drawings

PROCESS FOR PRODUCING 1,3-BIS(3-AMINOPHENOXY)BENZENE

This application is a 371 of PCT/JP02/01183 filed Feb. 13, 2002.

TECHNICAL FIELD

The present invention relates to a process for producing 1,3-bis(3-aminophenoxy)benzene which is useful as a raw material for especially adhesive polyimide resin, and polyether-polyamines useful as a raw material for heat-resistant polymer, especially polyimide, as well as to an intermediate used for production of 1,3-bis(3-aminophenoxy)benzene.

BACKGROUND ART

As a process for producing 1,3-bis(3-aminophenoxy) benzene, a reaction between 1,3-dibromobenzene and an alkali metal salt of 3-aminophenol is described in U.S. Pat. No. 4,222,962. In the process, however, the reactivity of the second step is inferior and the yield is low at 65%.

Also in JP-A-03-255058 is described a process which comprises reacting 1,3,5-trichlorobenzene with an alkali metal salt of 3-aminophenol to form two ether linkages and then conducting hydrogenolysis using a noble metal catalyst to eliminate the remaining chloro group. In the process described in the literature, however, trichlorobenzene into which electron-attractive chloro group is introduced excessively, is used in order to enhance the reactivity of chloro group substitution. This requires two steps and the process has not been satisfactory as an industrial process.

Further in J. Org. Chem., 1985, vol. 50 (No. 11), p. 1876 is described, as a similar reaction, a nucleophilic substitution of 1,2-difluorobenzene using a sodium salt of 2,2,2-trifluoroethanol. However, the di-substitution does not proceed at 90° C. and, even when the reaction temperature is increased up to 120° C., the yield of the di-substitution product is only 7%.

Also in Zu. Org. Khim., 1987, Vol. 23 (No. 6), p.1230 is described a reaction for obtaining 1,2-dimethoxybenzene from 1,2-difluorobenzene. However, the yield is only 6% even when a particular rhodium catalyst is used.

In view of the above prior art, production of 1,3-bis(3-aminophenoxy)benzene directly from 1,3-difluorobenzene and 3-aminophenol at a high yield is considered to be difficult.

In fact, there is found no example of production of 1,3-bis(3-aminophenoxy)benzene from 1,3-difluorobenzene and an alkali metal salt of 3-aminophenol. There is found no example, either, of reaction of 1,3-difluorobenzene with other phenol.

DISCLOSURE OF THE INVENTION

In view of the above situation, the present invention aims at providing a process for producing 1,3-bis(3-aminophenoxy)benzene, which is useful industrially.

The present inventors made a study on the production of 1,3-bis(3-aminophenoxy)benzene from 1,3-difluorobenzene and an alkali metal salt of 3-aminophenol. As a result, it was found out that the substitution reaction is a successive reaction and the intended product can be produced unexpectedly at a high yield via 1-(3-aminophenoxy)-3-fluorobenzene which is an intermediate.

It was also found out that the reaction time can be shortened significantly when, as the alkali metal, a sodium salt- and a potassium salt are used in combination. Based on these findings, the present invention has been completed.

According to the present invention, there is provided a process for producing 1,3-bis(3-aminophenoxy)benzene, which comprises reacting 1,3-difluorobenzene with an alkali metal salt of 3-aminophenol.

It is preferred to use, as the alkali metal salt, a sodium salt and a potassium salt in combination.

The reaction temperature is preferably 150 to 280° C.

The intermediate of the reaction is preferably 1-(3-aminophenoxy)-3-fluorobenzene.

By employing the above reaction, 1,3-bis(3-aminophenoxy)benzene can be produced from 1,3-difluorobenzene and 3-aminophenol directly in one step at a high yield.

BEST MODE FOR CARRYING OUT THE INVENTION

The present invention is described in detail below.

The alkali metal salt of 3-aminophenol, used in the present invention is preferably a sodium salt or a potassium salt. It is easily prepared by a reaction between 3-aminophenol and sodium hydroxide, potassium hydroxide, an alkali metal salt (e.g. sodium carbonate, sodium hydrogencarbonate, potassium carbonate or potassium hydrogencarbonate), or an alkali metal alcholate (e.g. sodium methylate or potassium t-butoxide).

The use amount of the alkali metal salt of 3-aminophenol is preferably 2 times or more, more preferably 2.1 times or more the moles of 1,3-difluorobenzene. Meanwhile, the amount is preferably 10 times or less, more preferably 5 times or less the moles of 1,3-difluorobenzene. When the amount is less than the above, some fluoro groups remain unsubstituted and it is impossible to achieve an object of converting all the fluoro groups into ether linkages. An amount more than the above is uneconomical.

When a sodium salt and a potassium salt both of 3-aminophenol are used in combination, the reaction time can be shortened significantly. Their proportions are preferably 9/1 to 1/9, more preferably 7/3 to 3/7 in terms of the molar ratio of sodium salt/potassium salt.

As the solvent, there can be used, for example, aprotic polar solvents such as acetonitrile, N-methylformamide, N,N-dimethylformamide, N,N-dimethylacetamide, dimethyl sulfoxide, dimethyl sulfone, sulfolane, N-methylpyrrolidone, 1,3-dimethyl-2-imidazolidinone (hereinafter abbreviated to DMI) and the like of these, preferred are N,N-dimethylformamide, dimethyl sulfoxide, sulfolane and DMI.

The use amount of the solvent is not particularly restricted. However, it is preferably 0.5 time or more, more preferably 1.0 time or more the mass of 3-aminophenol. Meanwhile, the amount is preferably 10 times or less, more preferably 5.0 times or less the mass of 3-aminophenol.

The reaction temperature is preferably 150° C. or more, more preferably 180° C. or more. Meanwhile, the temperature is preferably 280° C. or less, more preferably 240° C. or less. When the temperature is lower than the above, the reaction is significantly slow and not practical. When the temperature is too high, the alkali metal salt of 3-aminophenol is decomposed.

These reactions are carried out by using an autoclave if necessary, and the reaction time is 5 to 100 hours.

The preparation of an alkali metal salt of 3-aminophenol and its reaction with 1,3-difluorobenzene are preferably carried out in a nitrogen atmosphere in order to prevent the oxidation of 3-aminophenol and an intended product. Since the presence of water invites formation of impurities, it is preferred that the alkali metal salt is dehydrated, if necessary, to a minimum level by a means such as azeotropic dehydration or the like.

After the completion of the reaction, the reaction mixture is subjected to extraction with an organic solvent and then the solvent is distilled off for concentration, or the reaction mixture is discharged into water. The resulting crude product is purified by an ordinary method such as recrystallization, distillation, column chromatography or the like.

The present invention is specifically described below by way of Examples. However, the present invention is in no way restricted to these Examples alone. Incidentally, the reagents, etc. used were commercial high-purity products, unless otherwise specified.

EXAMPLE 1

Into a 500-mL four-necked flask provided with a stirrer, a reflux condenser and a Dean-stark trap were fed 71.5 g (0.655 mole) of 3-aminophenol, 53.5 g (0.655 mole) of an aqueous solution containing 49% by mass of sodium hydroxide, 250 g of DMI and 50 g of toluene. The flask contents were heated to 180° C. with stirring while nitrogen was passed through, to give rise to azeotropy to remove toluene and water. Then, the flask contents were cooled to room temperature and transferred into a 600-mL autoclave provided with a stirrer.

Next, 34 g (0.298 mole) of 1,3-difluorobenzene was added; the reactor was closed; its inside was purged with nitrogen; then, the autoclave was heated to 200° C.; and a reaction was allowed to take place at 200° C. for 53 hours. Then, the autoclave was cooled and part of the reaction mixture was analyzed by high-performance liquid chromatography (hereinafter abbreviated to HPLC). As a result, the yield of 1,3-bis(3-aminophenoxy)benzene was 82% (relative to 1,3-difluorobenzene).

EXAMPLE 2

Example of Combination Use of Sodium Salt and Potassium Salt

Into a 500-mL four-necked flask provided with a stirrer, a reflux condenser and a Dean-Stark trap were fed 71.5 g (0.655 mole) of 3-aminophenol, 26.7 g (0.327 mole) of an aqueous solution containing 49% by mass of sodium hydroxide, 19.3 g (0.327 mole) of moist pellets containing 95% by mass of potassium hydroxide, 250 g of DMI and 50 g of toluene. The flask contents were heated to 180° C. with stirring while nitrogen was passed through, to give rise to azeotropy to remove toluene and water. Then, the flask contents were cooled to room temperature and transferred into a 600-mL autoclave provided with a stirrer.

Next, 34 g (0.298 mole) of 1,3-difluorobenzene was added; the reactor was closed; its inside was purged with nitrogen; then, the autoclave was heated to 200° C.; and a reaction was allowed to take place at 200° C. for 19 hours. Then, the autoclave was cooled and part of the reaction mixture was analyzed by high-performance liquid chromatography. AS a result, 1,3-bis(3-aminophenoxy)benzene was formed at a yield of 87.9 mole % (relative to 1,3-difluorobenzene).

Further, the reaction mixture was filtered to remove inorganic salts, after which DMI was removed by distillation under vacuum to obtain a tar-like material. This tar-like material was subjected to vacuum distillation (distillation conditions: 1 mmHg, 300° C.) to obtain 72.7 g of 1,3-bis (3-aminophenoxy)benzene of 99.8% purity (by HPLC).

EXAMPLE 3

1-(3-Aminophenoxy)-3-fluorobenzene

Into a 500-mL four-necked flask provided with a stirrer, a reflux condenser and a Dean-stark trap were fed 71.5 g (0.655 mole) of 3-aminophenol, 53.5 g (0.655 mole) of an aqueous solution containing 49% by mass of sodium hydroxide, 250 g of DMI and 50 g of toluene. The flask contents were heated to 180° C. with stirring while nitrogen was passed through, to give rise to azeotropy to remove toluene and water. Then, the flask contents were cooled to room temperature and transferred into a 600-mL autoclave provided with a stirrer.

Next, 34 g (0.298 mole) of 1,3-difluorobenzene was added; the reactor was closed; its inside was purged with nitrogen; then, the autoclave was heated to 200° C.; a reaction was allowed to take place at 200° C. for 2 hours and discontinued. The reaction mixture was cooled and part thereof was analyzed by HPLC. As a result, the yield of 1-(3-aminophenoxy)-3-fuorobenzene was 85.8% (relative to 1,3-difluorobenzene) and the yield of 1,3-bis(3-aminophenoxy)benzene bis (3-aminophenoxy) benzene was 7.5% (relative to 1,3-difluorobenzene). 1,3-Difluorobenzene as a raw material remained by 4.9%.

The reaction mass was filtered, followed by washing with toluene. To the washings was added 300 g of toluene. The mixture was repeatedly washed using 300 g of water. The organic layer was concentrated to obtain 63.2 g of an oily material. Then, the oily material was purified by silica gel column chromatography (ethyl acetate:hexane=3:7) to obtain 44.1 g of 1-(3-aminophenoxy)-3-fluorobenzene as an oily material.

The results of identification are shown below.
$^1$H-NMR (DMSO-d6): δ

5.27 (S, 2H), 6.17–6.19 (D, 1H), 6.24 (S, 1H), 6.38–6.40 (D, 1H);

6.79–6.81 (M, 2H), 6.92 (T, 1H), 7.01–7.05 (T, 1H), 7.37–7.39 (Q, 1H)

$^{13}$C-NMR (DMSO-d6): δ

104.2, 105.4–105.6 (d), 106.2, 109.4–109.6 (d), 110.0, 114.0–114.1 (d);

130.2, 131.0–131.1 (d), 150.6, 156.7, 158.6–158.7 (d), 161.6–164.0 (d)

INDUSTRIAL APPLICABILITY

According to the present invention, 1,3-bis(3-aminophenoxy)benzene aminophenoxy)benzene can be produced in one step at a high yield.

What is claimed is:

1. A process for producing 1,3-bis(3-aminophenoxy) benzene, which comprises reacting 1,3-difluorobenzene with an alkali metal salt of 3-aminophenol.

2. A process for producing 1,3-bis(3-aminophenoxy) benzene according to claim 1, wherein a sodium salt and a potassium salt are used in combination as the alkali metal salt.

3. A process for producing 1,3-bis(3-aminophenoxy) benzene according to claim 1, wherein the reaction temperature is 150 to 280° C.

4. A process for producing 1,3-bis(3-aminophenoxy) benzene according to claim 1, wherein the intermediate of the reaction is 1-(3-aminophenoxy)-3-fluorobenzene.

* * * * *